(12) United States Patent
Wells et al.

(10) Patent No.: US 8,211,282 B2
(45) Date of Patent: *Jul. 3, 2012

(54) ELECTROCHEMICAL SENSOR

(75) Inventors: Steven Wells, Huntington Beach, CA (US); Gert Burkhardt, Pasadena, CA (US); Anthony Thai, Orange, CA (US)

(73) Assignee: Georg Fischer Signet, LLC, El Monte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/883,115

(22) Filed: Sep. 15, 2010

(65) Prior Publication Data

US 2011/0220497 A1    Sep. 15, 2011

Related U.S. Application Data

(63) Continuation of application No. 11/681,787, filed on Mar. 5, 2007, now Pat. No. 7,799,193.

(51) Int. Cl.
*G01N 27/40* (2006.01)
*G01N 27/401* (2006.01)

(52) U.S. Cl. ............ 204/433; 204/400; 204/228.5; 204/435

(58) Field of Classification Search ........ 204/228.6, 204/400, 433, 435
See application file for complete search history.

(56) References Cited

U.S. PATENT DOCUMENTS

| | | | |
|---|---|---|---|
| 4,112,352 A * | 9/1978 | Barben, II | 324/450 |
| 4,128,468 A | 12/1978 | Bukamier | |
| 4,235,688 A | 11/1980 | Sudrabin et al. | |
| 5,145,565 A | 9/1992 | Kater | |
| 5,147,524 A | 9/1992 | Broadley | |
| 5,152,882 A | 10/1992 | Benton | |
| 5,346,606 A | 9/1994 | Christner et al. | |
| 5,630,921 A | 5/1997 | Hess et al. | |
| 6,054,031 A | 4/2000 | Benton | |
| 6,416,653 B1 | 7/2002 | Barben, II et al. | |
| 6,423,197 B1 | 7/2002 | Lenferink et al. | |
| 2002/0043095 A1 | 4/2002 | Mason et al. | |
| 2004/0195098 A1 | 10/2004 | Broadley et al. | |

OTHER PUBLICATIONS

"pH Theory and Measurement", *Barben Analyzer Technology, LLC*, Carson City, NV ,, (earlier than Jun. 2006), pp. 1-11.
"Sensor Evolution", *Barben Analyzer Technology, LLC*, Carson City, NV, 5 pages, (earlier than Jun. 2006), pp. 4-5.
Spiegler, K. S., "Determination of Resistance Factors of Porous Diaphragms and Electrodes", *Electrochemical Society*, vol. 113, No. 2, 0013-4651, (1966), pp. 161-165.

* cited by examiner

*Primary Examiner* — Keith Hendricks
*Assistant Examiner* — Susan D Leong
(74) *Attorney, Agent, or Firm* — Tsircou Law, P.C.

(57) ABSTRACT

An electrochemical sensor is provided that includes a housing having an outer wall, a plurality of longitudinal chambers disposed within the outer wall, and a reference chamber housing a reference electrode. Ionic communication between the target fluid and the reference electrode must pass sequentially through each of longitudinal chambers from a first longitudinal chamber to the reference chamber. In this manner, the sensor provides generally a long, tortuous flow path, or salt bridge, between the target fluid and the reference electrode, resulting in a high resistance factor for the sensor.

20 Claims, 6 Drawing Sheets

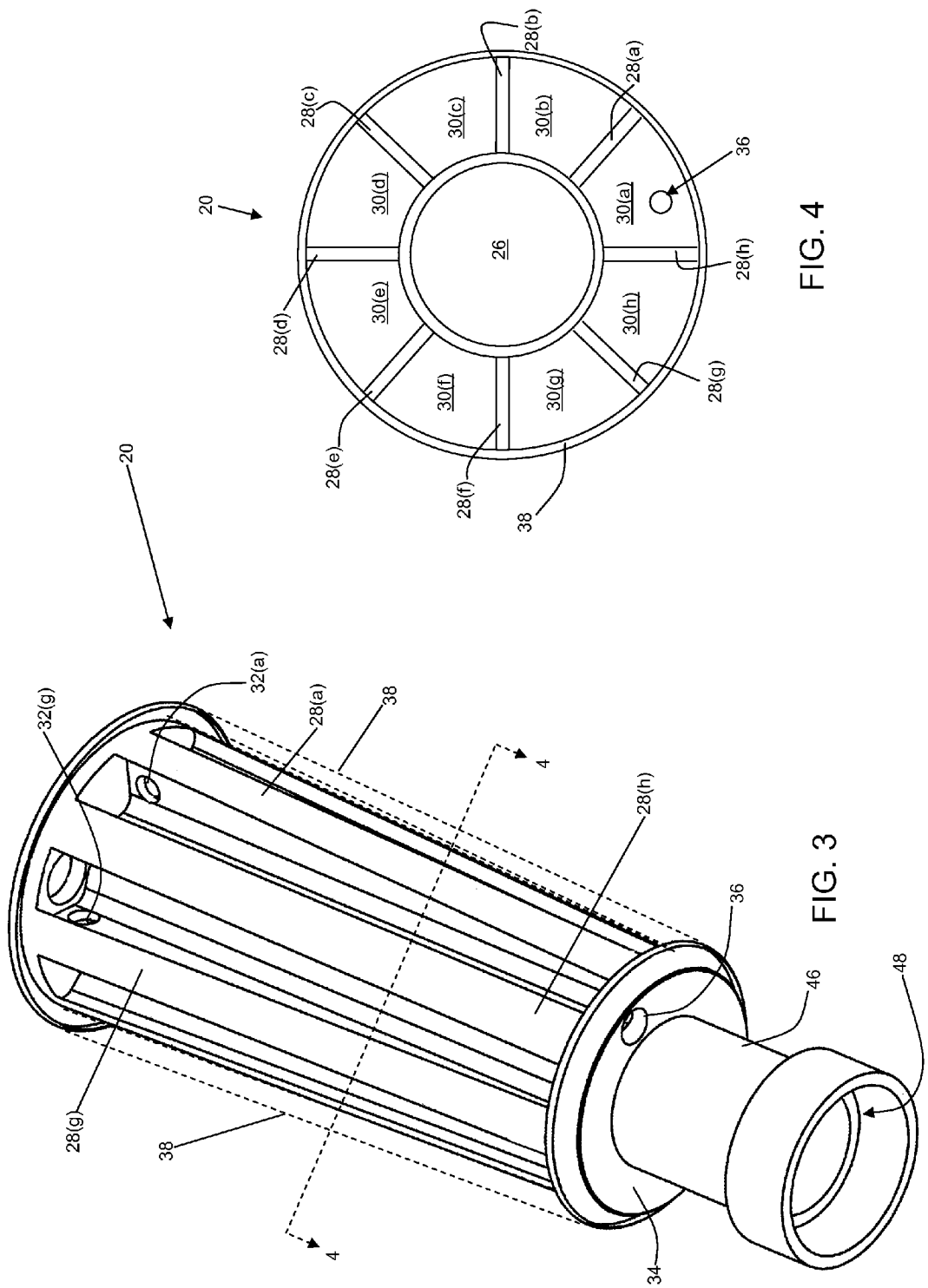

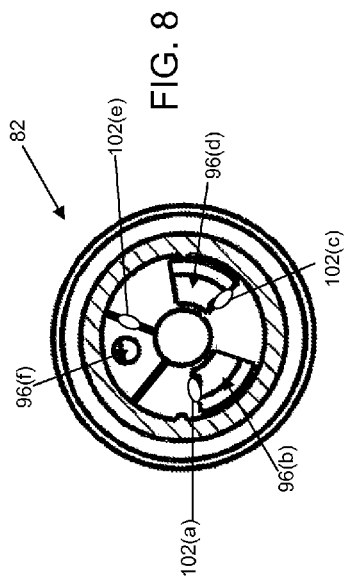
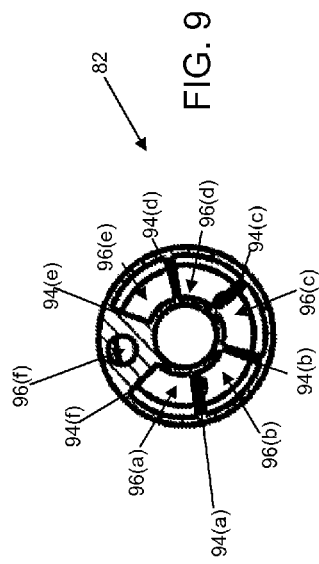
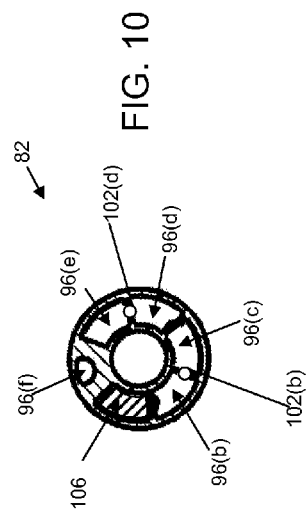
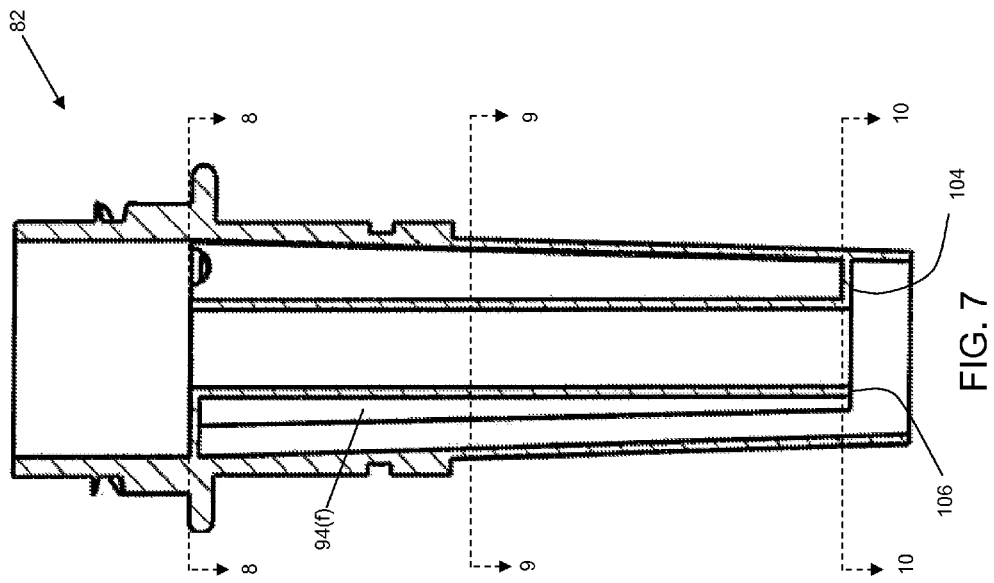

ELECTROCHEMICAL SENSOR

CROSS REFERENCE TO RELATED APPLICATION

This application is a continuation application of U.S. application Ser. No. 11/681,787, filed Mar. 5, 2007, which is herein incorporated by reference.

FIELD OF THE INVENTION

The present invention relates generally to electrochemical sensors and, more particularly, to such sensors having a reference electrode and a measuring electrode for measuring parameters of a target fluid.

BACKGROUND OF THE INVENTION

Electrochemical sensors have long been used to measure properties of fluids. Such sensors typically include a measuring electrode assembly and a reference electrode assembly, both which are electrically coupled to an instrument that senses the difference in electrical potential between the electrodes. In sensors of this kind, the measuring electrode assembly typically is exposed directly to the target fluid; whereas the reference electrode assembly is immersed in a stable electrolytic solution, i.e., a reference electrolyte. Sensors of this kind further include an ion-permeable separator, commonly referred to as liquid junction or salt bridge, disposed between the reference electrolyte and the target fluid, to enable a closed circuit between the electrodes.

In use, the measuring electrode generates a potential that varies as a function of prescribed parameters of the target fluid. The potential difference between the measuring electrode and the reference electrode provides a basis for measuring the prescribed parameters of the target fluid. For an accurate reading, the reference electrode must provide a stable potential.

The liquid junction plays an important role in achieving and maintaining a stable potential for the reference electrode. Ideally, the liquid junction should enable ionic communication between the reference electrolyte and the target fluid, while otherwise preventing transfer or intermingling of the fluids. Contamination or dilution of the reference electrolyte can unduly inhibit performance of the reference electrode, which is of particular concern when used in harsh chemical environments. The ability of the liquid junction to inhibit diffusion of the measured fluid, and ions therefrom, can be generally referred to as its resistance factor.

Much attention has been given to designing effective liquid junctions having a high resistance factor. Many approaches attempt to establish a tortuous path for ions through the junction by confining travel through relatively complex structural configurations that incorporate multiple components assembled together. For example, certain approaches include multiple layers held together with wood dowels. Other approaches utilize long path salt bridges for ionic communication between the liquid junction and the reference electrode, which generally require such sensors to have a relatively large sensor body, including housing length and diameter. Current approaches, particularly in industrial applications, often combine multiple tortuous path junctions connected by long path salt bridges.

Although generally effective, such approaches are relatively expensive and time-consuming to manufacture. Moreover, performance of such approaches can deteriorate with time.

It should be appreciated that there remains a need for an electrochemical sensor that addresses these concerns. The present invention fulfills this need and others.

SUMMARY OF THE INVENTION

In general terms, the present invention provides an electrochemical sensor having an outer wall, a plurality of longitudinal chambers disposed within the outer wall, and a reference chamber housing a reference electrode. Ionic communication between the target fluid and the reference electrode must pass sequentially through each of longitudinal chambers from a first longitudinal chamber to the reference chamber. In this manner, the sensor provides generally a long, tortuous flow path, or salt bridge, between the target fluid and the reference electrode, resulting in a high resistance factor for the sensor.

More particularly, in an exemplary embodiment, the housing further includes a bore for receiving a measuring electrode. The plurality of longitudinal walls are spaced in a radial manner about the bore, extending between the bore and the outer wall. The intermediate longitudinal chambers of the plurality of longitudinal chambers have wall apertures disposed at opposing ends thereof, such that ionic flow travels substantially the entire length of each of the intermediate longitudinal chambers.

The bore of the housing can further include a neck portion projecting from a base wall and terminating in a distal opening proximate to the distal end of the sensor assembly. The distal opening of the bore receives a proximate portion of a junction plug.

In a detailed aspect of an exemplary embodiment, the housing has an outer member and an inner member disposed within the outer member. The inner member includes the bore and the plurality of longitudinal walls. Either or both the outer member and the inner member can be formed of molded plastic.

In another exemplary embodiment, the housing includes a housing body formed of unitary construction. The housing body includes a bore for receiving a measuring electrode and the plurality of longitudinal walls. The housing body can further include a base wall disposed proximate to the junction plug. The base wall defines an aperture providing ionic communication between the junction plug and a first longitudinal chamber of the plurality of longitudinal chambers.

For purposes of summarizing the invention and the advantages achieved over the prior art, certain advantages of the invention have been described herein. Of course, it is to be understood that not necessarily all such advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment disclosed.

BRIEF DESCRIPTION OF THE DRAWINGS

Embodiments of the present invention will now be described, by way of example only, with reference to the following drawings in which:

FIG. 3 is a perspective view of the inner member of the housing the electrochemical sensor of FIG. 1, with portions of the outer wall in phantom.

FIG. 4 is a cross-sectional view of the inner member, taken along the line 4-4, of the inner member depicted in FIG. 3.

FIG. 7 is a cross-sectional view of the unitary housing body of the electrochemical sensor of FIG. 5, depicting an axial bore for receiving the measuring electrode and portions of an ionic path.

FIG. 8 is a cross-sectional view, taken along the line 8-8, of the unitary housing body depicted in FIG. 7.

FIG. 9 is a cross-sectional view, taken along the line 9-9, of the unitary housing body depicted in FIG. 7.

FIG. 10 is a cross-sectional view, taken along the line 10-10, of the unitary housing body depicted in FIG. 7.

DETAILED DESCRIPTION OF THE PREFERRED EMBODIMENTS

Figure 1:
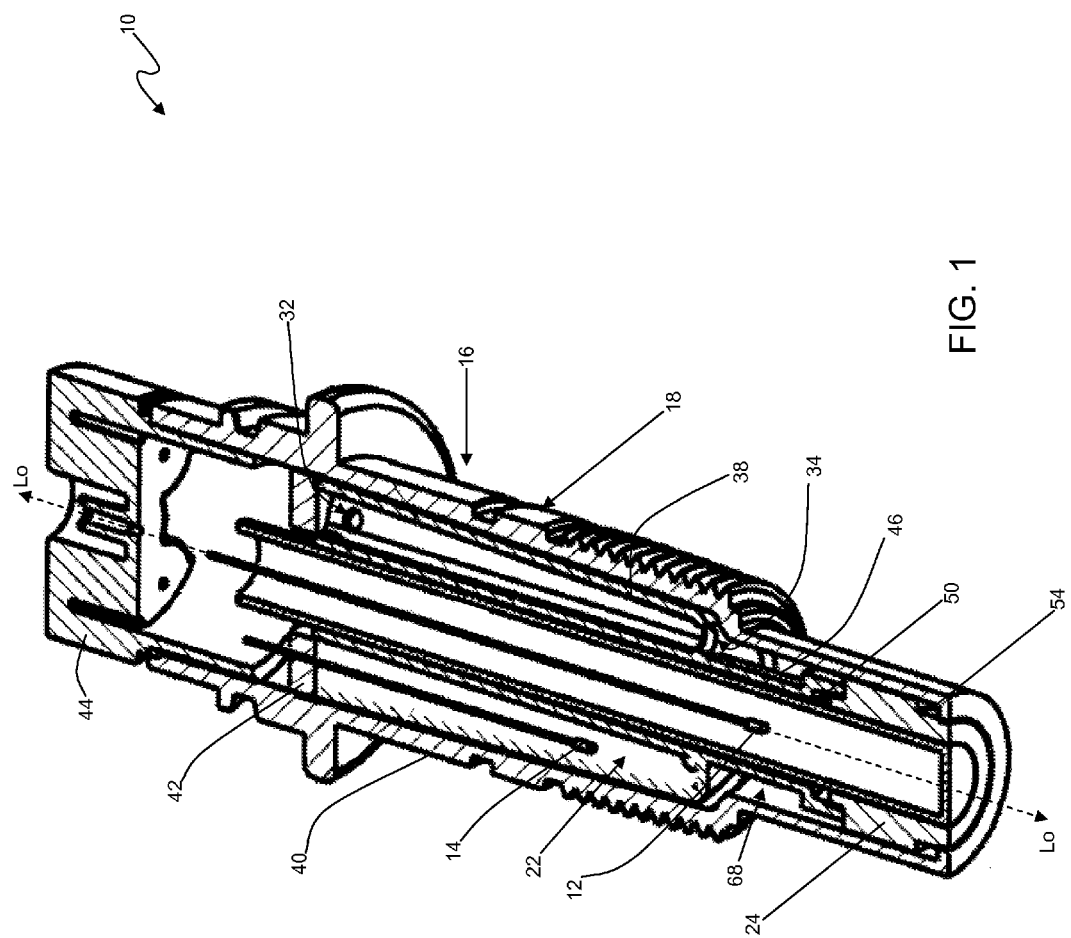
FIG. 1 is a cross-sectional view of a first embodiment of an electrochemical sensor in accordance with the present invention, depicting a reference electrode disposed within a cavity of a housing having an outer member and an inner member.
Figure 2:
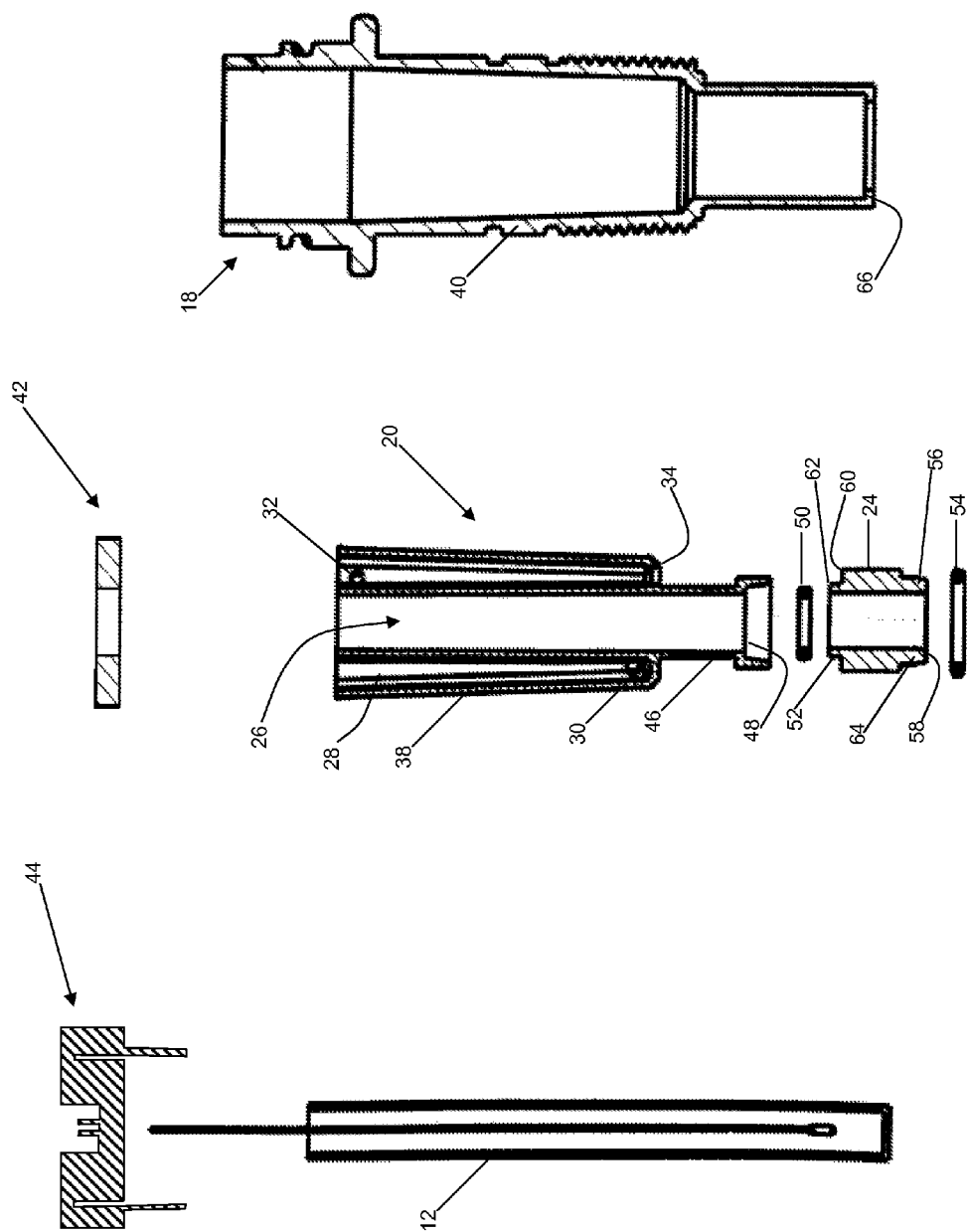
FIG. 2 is partially exploded view of the electrochemical sensor of FIG. 1, depicting selected components in cross section, including the inner and the outer members of the housing.

Referring now to the drawings, and particularly to FIGS. 1 and 2, there is shown an electrochemical sensor assembly 10, for measuring parameters of a target fluid (not shown), such as ORP or specific ions, e.g., pH or sodium. The sensor assembly 10 includes a measuring electrode 12 (e.g., glass pH electrode) and a reference electrode 14 coupled to a housing 16. The housing includes an outer member 18 and an inner member 20. The reference electrode is disposed within an electrolyte-filled reference chamber 22, defined by the inner member of the housing. The sensor assembly includes a liquid junction comprising a junction plug 24 disposed at a distal end of the housing. The inner member aids in defining a long, tortuous flow path, or salt bridge, between the target fluid and the reference electrode, requiring ionic flow to travel longitudinally and circumferentially about the housing, resulting in a high resistance factor for the sensor.

As best seen in FIGS. 3-4, the inner member 20 includes a generally cylindrical bore 26 configured to receive the measuring electrode 12 and further includes a plurality of longitudinal walls 28 radiating from the bore, defining a plurality of longitudinal chambers 30 disposed about the bore. More particularly, the inner member includes eight longitudinal walls 28($a$-$h$), defining eight longitudinal chambers 30($a$-$h$), of which one of the longitudinal chambers 30($h$) serves as the reference chamber 22, which includes the reference electrolyte. The inner member is configured such that ionic flow travels substantially the entire length of each longitudinal chamber, as the ionic flow circumscribes about the bore, passing sequentially through the longitudinal chambers from the first longitudinal chamber 30($a$) to the reference chamber 22.

The longitudinal chambers 30($a$-$h$) are connected via wall apertures 32($a$-$g$) defined by the longitudinal walls, with exception to the longitudinal wall 28($h$) between the reference chamber 22 and the first longitudinal chamber 30($a$). The wall apertures enable ionic flow between adjacent longitudinal chambers. The wall apertures of adjacent walls are disposed on opposing ends of the corresponding longitudinal chamber, requiring ionic flow to traverse the length of the corresponding chamber. Access to the first longitudinal chamber 30($a$) is provided by a base aperture 36 defined by the base wall 34 and the wall aperture 32($a$) at a proximal end of the first longitudinal chamber. Access to the reference chamber is limited to a single aperture, such that ionic flow terminates at the reference electrode 14.

In this manner, ionic flow traverses substantially the entire length of each of the longitudinal chambers, traveling longitudinally and circumferentially about the housing, from the first longitudinal chamber to the reference chamber 30($h$). Different number and spacing of the longitudinal walls can be used in other embodiments. For example, a sensor assembly can include at least three longitudinal walls to in excess of twenty longitudinal walls, as desired for particular embodiments. Moreover, in other embodiments, separate or additional wall structure can be used to define the reference chamber.

The inner member 20 of the housing 16 is disposed within the outer member 18 and is aligned with a longitudinal axis $L_o$ of the housing. The inner member 20 further includes an outer wall 38 disposed about the longitudinal walls 28($a$-$h$). The outer wall aids in defining the longitudinal chambers 30($a$-$h$) and is sized to snuggly contact a sidewall 40 of the outer member to inhibit liquid seepage therebetween. The sidewall of the outer member is generally equidistantly spaced from the bore about the circumference thereof.

Both the outer and the inner members (18, 20, respectively) are formed of molded plastic, such as polypropylene, PP, facilitating ease of manufacture and cost-effectiveness. In other embodiments, other materials can be used. Some examples of other materials that can be used include polyphenylsulfone PPS, polyvinyl chloride PVC, chlorinated polyvinyl chloride CPVC, polyvinyldiflouride PVDF, or other materials known in the art having appropriate chemical resistivity for a particular application.

The sensor assembly 10 further includes an upper seal 42 and a cap 44 disposed atop the proximal opening of the outer member 18. The upper seal is positioned above the inner member 20 and configured to engage the inner member and the sidewall 40 of the outer member 18 to provide a fluid tight seal, to confine the reference and bridge electrolytes.

With reference now to FIG. 2, the inner member 20 further includes a neck portion 46 of the bore 26. The neck portion projects from the base wall 34 of the inner member and terminates in a distal opening 48, proximate to the distal end of the sensor assembly 10. The distal opening defines an annular recess sized to receive a first o-ring 50 and a proximate portion 52 of the junction plug 24, to provide a secure seal to guard against contamination stemming from the target fluid or bridge solution in the stem or cavities. The sensor assembly 10 further includes a second o-ring 54 disposed about a distal portion 56 of the junction plug to engage the outer member 18 of the housing 16.

The junction plug 24 includes a distal surface 58 that is exposed directly to the target fluid and a proximal surface 60 confined within the housing 16. The junction plug defines a central passage that enables the measuring electrode 12 to contact the target fluid. As mentioned above, the junction plug is configured to engage the first and the second o-rings to ensure that ionic communication travels through the junction plug, between the distal and the proximal surfaces thereof. The first o-ring is received about a first annular projection 62 defined by the proximal surface, and the second o-ring is received about a second annular projection 64 defined by the distal surface.

A relatively small area of the proximal surface 60 is directly exposed to the electrolyte within the housing. In this embodiment, the exposed area of the proximal surface forms an annular region about the periphery of the junction plug, defined between the distal opening 48 of the inner member and the sidewall 40 of the outer member 18. In this manner, ionic communication between the target fluid and the reference electrolyte travels longitudinally through and radially across the junction plug. In other embodiments, portions of the junction plug exposed to the reference electrolyte can be provided in other configurations. Additional configurations are discussed in Applicants' co-pending U.S. patent application Ser. Nos. 11/533,989 and 11/564,015, filed Sep. 20, 2006 and Nov. 28, 2006, respectively, which are herein incorporated by reference for all purposes.

The junction plug 24 is formed of a unitary construction of porous ultra-high molecular weight polyethylene. In other embodiments, other materials having suitable characteristics can be used. For example, effective materials include ground glass, ceramic, other porous plastics, and wood. In addition, the liquid junction can be formed of multiple components and materials.

As seen in FIG. 1, the sensor assembly 10 defines a separation chamber 68 between the junction plug 24 and the base wall 34 of the inner member. In this embodiment, the separation chamber is generally cylindrical and is filled with reference electrolyte, facilitating ionic flow with the housing. In selected embodiments, a plug can be disposed within the separation chamber having characteristics of enabling ionic flow, while inhibiting contamination. Exemplary materials for the plug include ground glass, ceramic, other porous plastics, and wood.

The outer member 18 includes an inwardly facing flange 66 disposed about the distal opening thereof. The flange is sized such that the junction plug 24 and the second o-ring 54 can be securely seated in place proximate to the distal opening to contact the target fluid. The second o-ring is disposed about the junction plug to engage the sidewall 40 of the outer member and the inwardly facing flange 66, providing a secure seal about the plug. The first and the second o-rings ensure ionic communication occurs through the tortuous path of the junction plug and not through micro-gaps between the junction and the sidewall.

With reference again to FIG. 1, the reference electrode 14 is not directly exposed to the target fluid; rather it is surrounded by a reference electrolyte within the chamber 30(*h*) defined by the inner member 20 of the housing, enabling the reference electrode to provide a stable potential for comparison against the potential of the measuring electrode. The measuring electrode 12 and a reference electrode 14 are configured to be coupled to instrumentation, e.g., amplifier (not shown), to sense the potential difference between the measuring electrode and the reference electrode. Wires attached to the electrodes pass through the cap 44 to couple to the instrumentation.

In use, the end portion of the measuring electrode 12 is exposed to the target fluid such that the measuring electrode is electrochemically coupled to the target fluid. In the exemplary embodiment, a sensor assembly is configured to detect pH (e.g., a glass pH electrode), having a flat end. However, other embodiments can be configured to measure other parameters, individual or in combination. For example, oxidation-reduction potential (ORP), using a nobel metal electrode, or other types of specific ions can be measured including, for example, ammonium, bromide, chloride, fluoride, sulfide, nitrate, and sodium. In addition, measuring electrodes having various bulb-shaped ends can be used.

Referring again to FIG. 2, during assembly, the junction plug 24 is position about the distal end of the measuring electrode 12. The first and the second o-rings (50, 54) are positioned over the junction plug 24, as depicted. The inner member 20 is positioned over the measuring electrode so that the junction plug and the first o-ring is snug within the distal opening 48 of the bore 26. This combination is then received within the outer member 18.

Reference electrolyte is placed into the reference chamber along with the reference electrode. After appropriate conditioning, an electrolyte (salt bridge) solution is introduced throughout the longitudinal chambers and the junction plug 24. Various types of electrolytes can be used, singly or in combination, such as a potassium chloride/silver chloride (KCl/AgCl) mixture. The salt bridge and the reference solution may be hardened or gelled by a variety of agents, including epoxy blends and gelling agents. This can aid in slowing the ingress of ions from the target fluid. Optionally, different electrolytes can be used in the longitudinal or other chambers. Those skilled in the art will recognize that various reference systems may be used and that various electrolytes can be used as salt bridges. This invention is not necessarily limited by any particular reference or salt bridge composition.

Thereafter, the upper seal 42 and the cap 44 are also positioned in place. Adhesive material can be provided to secure the various components, as needed. Nonetheless, care should be taken to ensure that adhesive does not bar or excessively inhibit electrochemical communication between the target fluid and the reference electrode or electrochemically contaminate the electrodes or electrolytes.

Figure 5:
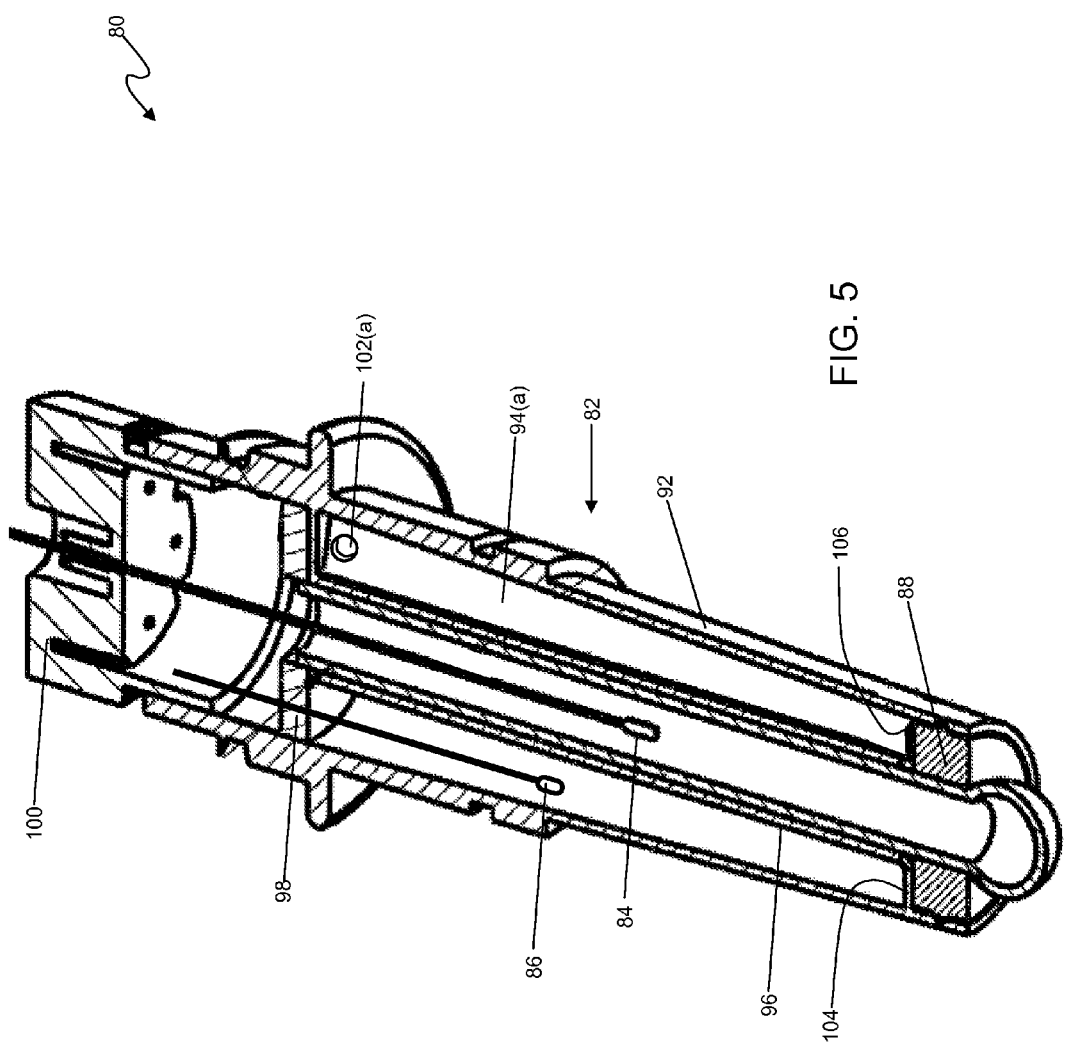
FIG. 5 is a cross-sectional view, similar to FIG. 1, of a second embodiment of an electrochemical sensor in accordance with the present invention, including a housing body of unitary construction.
Figure 6:
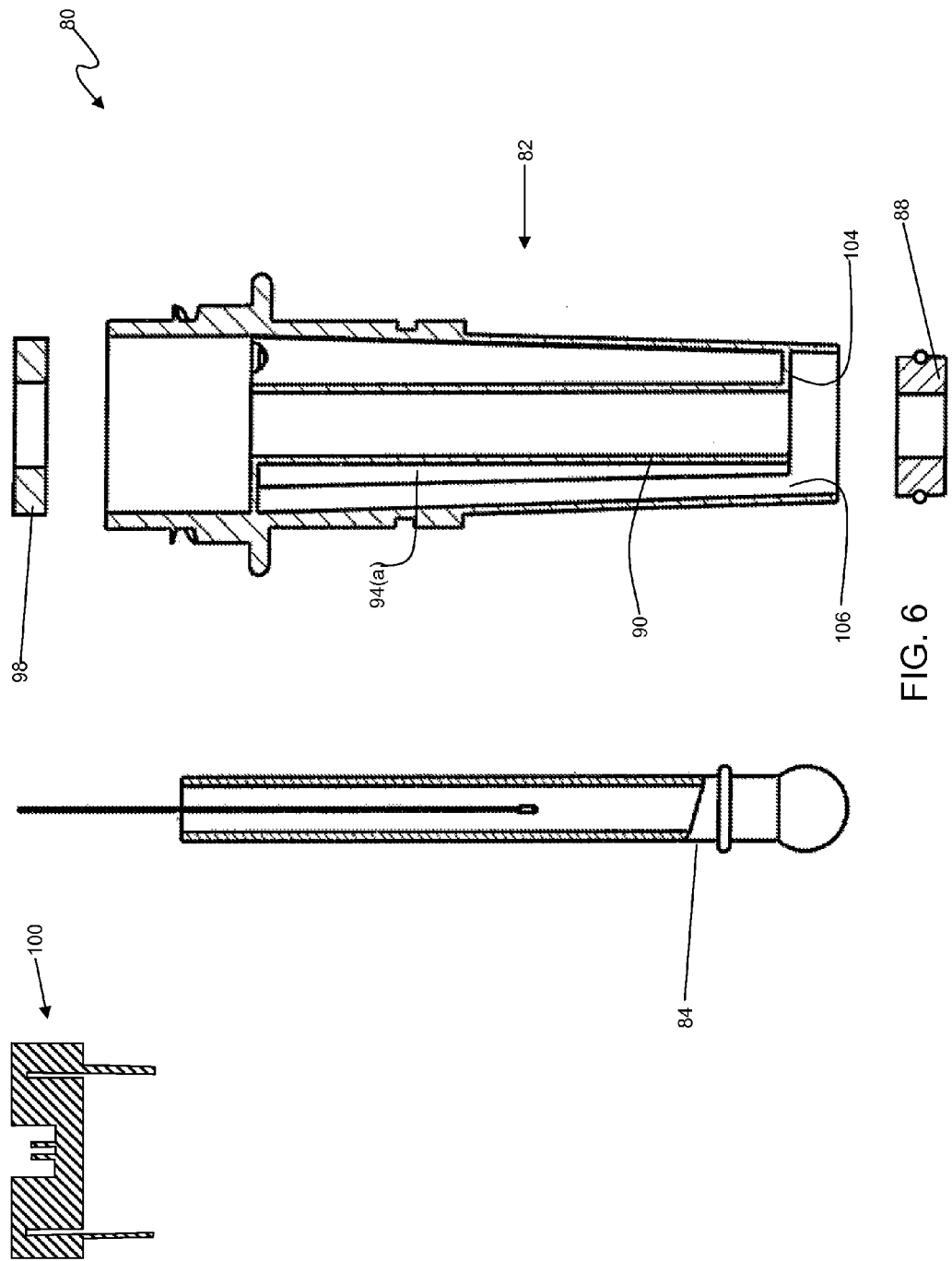
FIG. 6 is partially exploded view of the electrochemical sensor of FIG. 5, depicting components in cross section, including the unitary housing body, a measuring electrode, an upper seal, a junction plug, and a cap.

With reference to FIG. 5-6, a second embodiment of a sensor assembly 80 is shown, including a housing body 82, a measuring electrode 84, a reference electrode 86, and a junction plug 88. In this embodiment, the housing body is formed of unitary construction, including a bore 90, an outer wall 92, and a plurality of longitudinal walls 94 radiating axially between the bore and the outer wall. The longitudinal walls aid in defining a plurality of longitudinal chambers 96 disposed about the bore, of which one of the longitudinal chambers serves as a reference chamber 96(*f*) for receiving the reference electrode 86.

The sensor assembly 80 further includes an upper seal 98 disposed atop the longitudinal chambers 96 and a cap 100. The measuring electrode 84 and a reference electrode 86 are configured to be coupled to instrumentation, e.g., amplifier (not shown), to sense the potential difference between the measuring electrode and the reference electrode. Wires attached to the electrodes pass through the cap to couple to the instrumentation.

As best seen in FIGS. 7-10, the housing body 82 includes six longitudinal walls 94(*a-f*), defining six longitudinal chambers 96(*a-f*). In this embodiment, the reference chamber 96(*f*) is generally cylindrical. Each of the longitudinal walls defines an aperture 102 that enables ionic communication between adjacent longitudinal chambers, with exception to the longitudinal wall 94(*f*) between the reference chamber and the first longitudinal chamber 96(*a*). For each intermediate longitudinal chambers 96(*b-e*), the respective apertures are disposed at opposing ends of the chamber such that ionic communication must travel substantially the entire length thereof. Access to the reference chamber is limited to a single aperture. Access to the first longitudinal chamber 96(a) is provided by the base aperture defined by the base wall 104 and a base aperture 106 defined by a longitudinal wall at a distal end of the first longitudinal chamber. Accordingly, the housing body aids in defining a long, tortuous flow path, or salt bridge, between the target fluid and the reference electrode, resulting in a high resistance factor for the sensor.

The base wall 104 is disposed adjacent to the junction plug 88, such that ions must migrate axially through and transverse across the junction plug to pass through the aperture of the cross member, resulting in an increased effective path length through the junction plug.

In the exemplary embodiment, the base wall 104 defines a single hollow aperture, the base aperture 106. Preferably, the base wall covers between about 50 percent to about 98 percent of the proximal surface of the junction plug. In the exemplary embodiment, the base wall covers about 85 percent of the proximal surface of the junction plug.

Other configurations for the base wall can be used. For example, several apertures as well as other shapes, e.g., ring, rectangle, and so on, can be used. Moreover, in other embodiments, the base wall can be attached directly to the proximal surface of the cross member. Various aperture shapes can be combined in a single embodiment. Additional configurations are discussed in Applicants' co-pending U.S. patent applications, identified above.

The sensor assembly 80 excludes a separation chamber between the longitudinal chambers and the junction plug, as provided in the first embodiment, sensor assembly 10. However, other embodiments implementing a unitary housing body can provide a separation chamber, similar to that in the first embodiment.

In the exemplary embodiments discussed in detailed above, reference electrolyte is free to flow among longitudinal chambers. In other embodiments, porous barriers, e.g., aperture plugs, can be disposed in one or more of the wall apertures to retard contamination, while enabling ionic flow. Materials for such barriers include, for example, ground glass, ceramic, porous plastics, and wood. For example, in one approach, wood plugs or other suitable materials can be place in the walls apertures disposed adjacent to the proximal end of the inner member. In another approach, plugs can be placed in the longitudinal chambers. Such configurations can increase manufacturing costs but, nonetheless, can be beneficial, particularly in harsh chemical environments.

In addition, in the exemplary embodiments above, the apertures of the longitudinal walls are oriented generally perpendicular to the walls and extend generally linearly through the wall. In other embodiments, one or more of the wall apertures can implement alternate configurations. For example, wall apertures can be angled relative to perpendicular, can be multi-angled, or can otherwise have a nonlinear path through the corresponding wall.

It should be appreciated from the foregoing that the present invention provides an electrochemical sensor that includes a housing having an outer wall and a plurality of longitudinal chambers disposed within the outer wall, including a first chamber and a reference chamber. Ionic communication between the target fluid and the reference electrode passes sequentially through each of longitudinal chambers from a first longitudinal chamber to the reference chamber. In this manner, the sensor provides generally a long, tortuous flow path, or salt bridge, between the target fluid and the reference electrode, resulting in a high resistance factor for the sensor.

Although the invention has been disclosed in detail with reference only to the exemplary embodiments, those skilled in the art will appreciate that various other embodiments can be provided without departing from the scope of the invention. Accordingly, the invention is defined only by the claims set forth below.

What is claimed is:

1. An electrochemical sensor, comprising:
a housing including a proximal end and a distal end, the distal end configured to be proximate to a target fluid, thereby defining a longitudinal axis, the housing having an outer wall that circumscribes the housing, the housing defining a plurality of longitudinal chambers disposed within the confines of the outer wall of the housing in which the longitudinal chambers are aligned with the longitudinal axis, wherein the housing is configured to enable ionic communication to flow between the longitudinal chambers;
a reference electrode disposed within a reference chamber of the housing; and
a junction plug having a first surface configured to contact the target fluid and a second surface, the junction plug comprising a porous material that enables ionic flow through the junction plug from the first surface to the second surface;
wherein ionic communication between the target fluid and the reference electrode within the reference chamber must pass sequentially through the plurality of longitudinal chambers traveling in alternating longitudinal directions from a first longitudinal chamber to reach the reference chamber.

2. An electrochemical sensor as defined in claim 1, wherein intermediate longitudinal chambers of the plurality of longitudinal chambers have wall apertures disposed at opposing ends thereof, such that ionic flow travels substantially the entire length of each of the intermediate longitudinal chambers.

3. An electrochemical sensor as defined in claim 1, wherein the housing further comprising a bore for receiving a measuring electrode, the bore between the proximal end and the distal end of the housing.

4. An electrochemical sensor as defined in claim 3, wherein a plurality of longitudinal walls are disposed between the plurality of longitudinal chambers and are spaced in a radial manner about the bore, extending between the bore and the outer wall.

5. An electrochemical sensor as defined in claim 4, wherein the bore of the housing includes a neck portion projecting from a base wall and terminating in a distal opening proximate to the distal end of the sensor assembly.

6. An electrochemical sensor as defined in claim 4, wherein the distal opening of the bore receives a proximate portion of the junction plug.

7. An electrochemical sensor as defined in claim 4, wherein the housing has an outer member and an inner member disposed within the outer member, the inner member including the bore and the plurality of longitudinal walls.

8. An electrochemical sensor as defined in claim 7, wherein the inner member of the housing is formed of molded plastic.

9. An electrochemical sensor as defined in claim 4, wherein the housing includes a housing body formed of unitary construction, the housing body includes a bore for receiving a measuring electrode and the plurality of longitudinal walls.

10. An electrochemical sensor as defined in claim 9, wherein the housing body further includes a base wall disposed proximate to the junction plug, the base wall defines an aperture providing ionic communication between the junction plug and the first longitudinal chamber of the plurality of longitudinal chambers.

11. An electrochemical sensor, comprising:

a housing including a proximal end and a distal end, the distal end configured to be proximate to a target fluid, thereby defining a longitudinal axis, the housing having an outer wall that circumscribes the housing, the housing defining a plurality of longitudinal chambers disposed within the confines of the outer wall of the housing in which the longitudinal chambers are aligned with the longitudinal axis, wherein the housing is configured to enable ionic communication to flow between the longitudinal chambers, the housing having a base wall coupled to a distal end of the longitudinal chambers, the base wall defining a base aperture that enable ionic flow into a first chamber of the longitudinal chambers;

a reference electrode disposed within a reference chamber; and a junction plug disposed at the distal end of the housing, the plug having a first surface configured to contact the target fluid and a second surface in confronting relationship to the base wall, the junction plug comprising a porous material that enables ionic flow through the junction plug from the first surface to the second surface;

wherein ionic communication between the target fluid and the reference electrode within the reference chamber must pass sequentially through the plurality of longitudinal chambers traveling in alternating longitudinal directions from the first longitudinal chamber to reach the reference chamber.

12. An electrochemical sensor as defined in claim 11, wherein the housing further comprising a bore for receiving a measuring electrode.

13. An electrochemical sensor as defined in claim 12, wherein the bore of the housing includes a neck portion projecting from the base wall and terminating in a distal opening proximate to the distal end of the sensor assembly.

14. An electrochemical sensor as defined in claim 13, wherein the distal opening of the bore receives a proximate portion of the junction plug.

15. An electrochemical sensor, comprising:

a housing including a proximal end and a distal end, the distal end configured to be proximate to a target fluid, thereby defining a longitudinal axis, the housing having an outer wall that circumscribes the housing, the housing defining a plurality of longitudinal chambers disposed within the confines of the outer wall of the housing in which the longitudinal chambers are aligned with the longitudinal axis, wherein the housing is configured to enable ionic communication to flow between the longitudinal chambers;

a reference electrode disposed within a reference chamber of the housing; and a junction plug having a first surface configured to contact the target fluid and a second surface, the junction plug comprising a porous material that enables ionic flow through the junction plug from the first surface to the second surface;

wherein the housing configured such that ionic communication between the target fluid and the reference electrode within the reference chamber must pass sequentially through the plurality of longitudinal chambers traveling in alternating longitudinal directions with respect to adjacent longitudinal chambers from a first longitudinal chamber to reach the reference chamber.

16. An electrochemical sensor as defined in claim 15, wherein intermediate longitudinal chambers of the plurality of longitudinal chambers have wall apertures disposed at opposing ends thereof, such that ionic flow travels substantially the entire length of each of the intermediate longitudinal chambers.

17. An electrochemical sensor as defined in claim 15, wherein the housing further comprising a bore for receiving a measuring electrode, the bore between the proximal end and the distal end of the housing.

18. An electrochemical sensor as defined in claim 17, wherein a plurality of longitudinal walls are disposed between the plurality of longitudinal chambers.

19. An electrochemical sensor as defined in claim 18, wherein the housing includes a housing body formed of unitary construction, the housing body includes a bore for receiving a measuring electrode and the plurality of longitudinal walls.

20. An electrochemical sensor as defined in claim 19, wherein the housing body further includes a base wall disposed proximate to the junction plug, the base wall defines an aperture providing ionic communication between the junction plug and the first longitudinal chamber of the plurality of longitudinal chambers.

* * * * *